United States Patent [19]

Durand et al.

[11] Patent Number: 5,703,118

[45] Date of Patent: Dec. 30, 1997

[54] USE OF BENZOPYRAN DERIVATIVES FOR THE TREATMENT OF PATHOLOGIES ASSOCIATED WITH THE $NA^+$-INDEPENDENT $CI^-/HCO_3$-EXCHANGER

[75] Inventors: Ludovic Durand, Cholet; Jean-Paul Babingui, Nantes; Claudie Moulin, Nantes; Sylvie Robert-Piessard, Nantes; Guillaume Le Baut, Saint Sebastien Sur Loire; Elisabeth Scalbert, Boulogne; Daniel-Henri Caignard, Paris; Pierre Renard, Versailles, all of France

[73] Assignee: Adir et Compagnie, Courbevoie, France

[21] Appl. No.: 643,257

[22] Filed: May 3, 1996

[30]   Foreign Application Priority Data

May 5, 1995 [FR] France ................... 95 05361

[51] Int. Cl.⁶ ...................................................... A61K 31/35
[52] U.S. Cl. ............................................. 514/456; 514/925
[58] Field of Search .................................... 514/456, 821, 514/825, 866, 870, 925

[56]           References Cited

U.S. PATENT DOCUMENTS 5,315,017   5/1994   Le Baut et al. ................ 549/408

*Primary Examiner*—Kimberly Jordan
*Attorney, Agent, or Firm*—The Firm of Gordon W. Hueschen

[57]             ABSTRACT

A method of treating a mammal afflicted with a disorder associated with the $Na^+$-independent $Cl^-/HCO_3-$ exchanger comprising the step of administering a compound selected from those of formula (I):

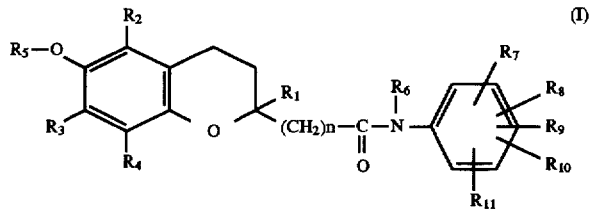

in which $R_1$, $R_2$, $R_3$, $R_4$, $R_5$, $R_6$, $R_7$, $R_8$, $R_9$, $R_{10}$, $R_{11}$ and n are as defined in the description, which is effective for alleviating the said disorder.

6 Claims, No Drawings

USE OF BENZOPYRAN DERIVATIVES FOR THE TREATMENT OF PATHOLOGIES ASSOCIATED WITH THE $Na^+$-INDEPENDENT $Cl^-/HCO_3^-$-EXCHANGER

The invention relates to the use of benzopyran derivatives for the production of pharmaceutical compositions intended for the treatment of pathologies associated with the $Na^+$-independent $Cl^-/HCO_3^-$ exchanger.

The $Na^+$-independent $Cl^-/HCO_3^-$ exchanger ("anion exchanger", referred to hereinbelow as "AE") catalyses a release of bicarbonate ion $HCO_3^-$ from the cell against an uptake of chloride $Cl^-$ into the cell. This exchange is electrically neutral.

This exchanger is known to be involved, in particular, in the regulation of the intracellular pH, the cell volume and the intracellular chloride ($Cl^-$) concentration. However, in erythrocytes, it also plays a very specific role by allowing the transport of $CO_2$ from the cells to the lungs in the form of plasma $HCO_3^-$.

As regards the regulation of the intracellular pH, this exchanger constitutes the only physiological process of extrusion outside the cell of basic equivalents mediated by a protein whose molecular structure is known. It is generally activated by intracellular alkalosis.

The prototype of the $Na^+$-independent $Cl^-/HCO_3^-$ exchanger, referred to as "AE1" was initially demonstrated in the erythrocyte membrane, but has served as a basis for the identification of two other genes coding for "AE2" and "AE3". AE1, AE2 and AE3 have a homology of 80% at the level of their —COOH terminal membrane part (part essential for the functioning of the exchanger) and also have a very considerable specificity of tissue expression (Alper S. L. Cell. Physiol. Biochem. 1994, 4: 265–281).

The inhibition of the AE exchanger in cardiomyocytes is beneficial during myocardial ischaemia in order to prevent intracellular acidosis (by intracellular retention of $HCO3^-$) and its ionic ($Na^+$ and $Ca^{++}$) and metabolic consequences. Indeed, evers though theoretically, the AE (AE3 type) of the cardiomyocyte is required to be activated essentially by intracellular alkalosis, it has recently been shown that this AE is activated by purinergic or $\beta_1$-adrenergic stimulation, thus generating intracellular acidification (Pucéat M. et al., J. Physiol., 1991, 444: 241–256; Désilets M. et al., Circ Res, 1994, 75: 862–869). During a myocardial ischaemia, the concentrations of the mediators are generally increased (eg.: catecholamines, ATP and angiotensin II) and bring about, in this case, a hyperactivation of the cardiomyocytic AE, which contributes towards the acidification which is harmful to the cell integrity as the complement of the metabolic acidification already present during ischaemia.

The invention relates to the use of the compounds of formula (I):

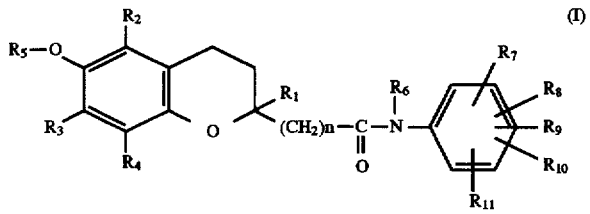

in which n represents 0 or 1, $R_1$, $R_2$, $R_3$ and $R_4$, which are identical or different, represent, independently of each other, a hydrogen or an alkyl;

$R_5$ represents a hydrogen or a radical chosen from alkyl, alkylcarbonyl, alkoxyalkyl, alkoxycarbonyl, alkoxycarbonylalkyl and carboxyalkyl;

$R_6$ represents a hydrogen or a radical chosen from alkyl, phenyl and phenylalkyl;

$R_7$, $R_8$ and $R_9$ represent, independently of each other, a radical chosen from halogen, alkyl, alkyl substituted with one or more halogens, alkoxy, hydroxyl, alkoxycarbonyl and carboxyl;

and $R_{10}$ and $R_{11}$ represent, independently of each other, a hydrogen or a radical chosen from halogen, alkyl, alkyl substituted with one or more halogens, alkoxy, hydroxyl, alkoxycarbonyl and carboxyl;

the enantiomers and diastereoisomers thereof and the addition salts thereof with a pharmaceutically acceptable base, it being understood that the terms "alkyl" and "alkoxy" denote linear or branched groups of 1 to 8 carbon atoms, for the production of pharmaceutical compositions intended for the prevention and treatment of disorders associated with the $Na^+$-independent $Cl^-/HCO_3^-$ exchanger.

More particularly, the invention relates to the use, for the production of pharmaceutical compositions intended for the prevention and treatment of pathologies associated with the $Na^+$-independent $Cl^-/HCO_3^-$ exchanger, of the compounds of formulae (I) in which, taken together or separately, where appropriate:

n represents 0, n represents 1, $R_1$, $R_2$, $R_3$, and $R_4$ represent an alkyl, $R_5$ represents a hydrogen, $R_5$ represents an acetyl, $R_6$ represents a hydrogen, and $R_{10}$ and $R_{11}$ represent a hydrogen, the enantiomers and diastereoisomers thereof and the addition salts thereof with a pharmaceutically acceptable base.

In particular, the alkyl radicals present in the formula (I) may be chosen from methyl, ethyl, n-propyl, isopropyl, n-butyl, isobutyl, sec-butyl, tert-butyl, pentyl, hexyl, heptyl and octyl, for example methyl.

The alkoxy radicals present in the formula (I) may be chosen from methoxy, ethoxy, n-propoxy, isopropoxy, n-butoxy, iso-butoxy, sec-butoxy, tert-butoxy, pentyloxy, hexyloxy, heptyloxy and octyloxy, and the halogens present in the formula (I) may be chosen from bromine, chlorine, fluorine and iodine.

For example, the invention relates to the use, for the production of pharmaceutical compositions intended for the prevention and treatment of pathologies associated with the $Na^+$-independent $Cl^-/HCO_3^-$ exchanger, of the compounds of formula (I) corresponding to the formulae (I/a) and (I/b), specific cases of the compounds of formula (I):

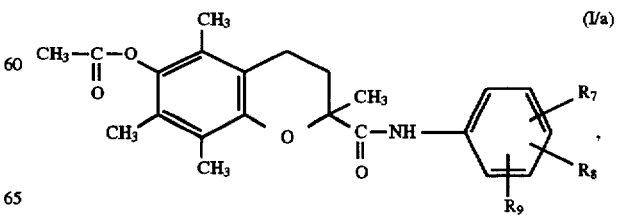

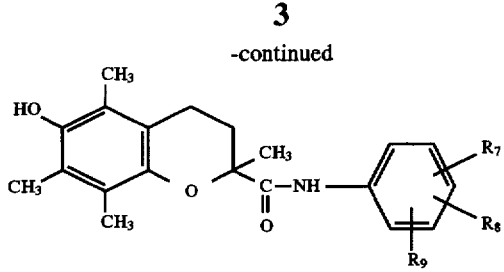

the enantiomers and diastereoisomers thereof, and the addition salts thereof with a pharmaceutically acceptable base.

For example, the invention relates to the use according to the invention of compounds chosen from 1) N-(2,4,6-trimethylphenyl)-(6-acetoxy-3,4-dihydro-2,5,7,8-tetramethyl-2H[1]-benzopyran-2-yl)carboxamide Melting point: 148°–149° C.
2) N - (2,4,6-trimethylphenyl)-(6-hydroxy-3,4-dihydro-2,5,7,8-tetramethyl-2H [1]-benzopyran-2-yl) carboxamide Melting point: 163°–164° C.
3) N-(3,4,5-trimethoxyphenyl)-(6-acetoxy-3,4-dihydro-2,5,7,8-tetramethyl-2H[1]-benzopyran-2-yl) carboxamide Melting point: 65°–68° C.
4) N-(3,4,5-trimethoxyphenyl)-(6-hydroxy-3,4-dihydro-2,5,7,8-tetramethyl-2H[1]-benzopyran-2-yl) carboxamide Melting point: 154°–156° C.
5) N-(4-hydroxy-2,3-dimethylphenyl)-(6-acetoxy-3,4-dihydro-2,5,7,8-tetramethyl-2H [1]benzopyran-2-yl) carboxamide Melting point: 230°–232° C.
6) N-(4-hydroxy-2,3-dimethylphenyl)-(6-hydroxy-3,4-dihydro-2,5,7,8-tetramethyl-2H[1]-benzopyran-2-yl) carboxamide Melting point: 182°–183° C.
7) N-(2-carboxy-4,5-dimethoxyphenyl)-(6-acetoxy-3,4-dihydro-2,5,7,8-tetramethyl-2H[1]-benzopyran-2-yl) carboxamide Melting point: 254°–256° C.
8) N-(2-carboxy-4,5-dimethoxyphenyl)-(6-hydroxy-3,4-dihydro-2,5,7,8-tetramethyl-2H[1]-benzopyran-2-yl) carboxamide Melting point: 244° C.
9) N-(3,5-dichloro-4-hydroxyphenyl)-(6-acetoxy-3,4-dihydro-2,5,7,8-tetramethyl-2H[1]-benzopyran-2-yl) carboxamide Melting point: 168° C.
10) N-(3,5-dichloro-4-hydroxyphenyl)-(6-acetoxy-3,4-dihydro-2,5,7,8-tetramethyl-2H[1]-benzopyran-2-yl) carboxamide Melting point: 208° C.
11) N-(2-carboxy-4,6-dimethylphenyl)-(6-acetoxy-3,4-dihydro-2,5,7,8-tetramethyl-2H[1]-benzopyran-2-yl) carboxamide
12) N-(2-carboxy-4,6-dimethylphenyl)-(6-acetoxy-3,4-dihydro-2,5,7,8-tetramethyl-2H[1]-benzopyran-2-yl) carboxamide Melting point: 244° C.
13) N-(2,4,5-trimethylphenyl)-(6-acetoxy-3,4-dihydro-2,5,7,8-tetramethyl-2H [1]-benzopyran-2-yl) carboxamide Melting point: 160°–162° C.
14) N-(2,4,5-trimethylphenyl)-(6-hydroxy-3,4-dihydro-2,5,7,8-tetramethyl-2H[1]-benzopyran-2-yl) carboxamide Melting point: 180°–182° C.
15) N-(3,4,5-trimethoxyphenyl)-(6-acetoxy-3,4-dihydro-5,7,8-trimethyl-2H [1]-benzopyran-2-yl)carboxamide
16) N-(3,4,5-trimethoxyphenyl)-(6-hydroxy-3,4-dihydro-5,7,8-trimethyl-2H [1]-benzopyran-2-yl)carboxamide Melting point: 174°–175° C.
17) N-(3,4,5-trimethoxyphenyl)-(6-acetoxy-7-tert-butyl-3,4-dihydro-2-methyl-2H [1]-benzopyran-2-yl) carboxamide
18) N-(3,4,5-trimethoxyphenyl)-(6-hydroxy-7-tert-butyl-3,4-dihydro-2-methyl-2H [1]-benzopyran-2-yl) carboxamide Melting point:212°–213° C.
19) N-(3,4,5-trimethoxyphenyl)-(6-acetoxy-7-tert-butyl-3,4-dihydro-2-methyl-2H [1]-benzopyran-2-yl) acetamide
20) N-(3,4,5-trimethoxyphenyl)-(6-hydroxy-7-tert-butyl-3,4-dihydro-2-methyl-2H [1]-benzopyran-2-yl) acetamide Melting point: 167°–168° C.
21) N-(3,5-di-tert-butyl-4-hydroxyphenyl)-(6-acetoxy-3,4-dihydro-2,5,7,8-tetramethyl-2H [1]-benzopyran-2-yl)carboxamide
22) N-(3,5-di-tert-butyl-4-hydroxyphenyl)-(6-hydroxy-3,4-dihydro-2,5,7,8-tetramethyl-2H [1]-benzopyran-2-yl)carboxamide Melting point: 172°–174° C.
23) N-(2,4,5-trimethylphenyl)-(6-acetoxy-3,4-dihydro-5,7,8-trimethyl-2H [1]-benzopyran-2-yl)carboxamide
24) N-(2,4,5-trimethylphenyl)-(6-hydroxy-3,4-dihydro-5,7,8-trimethyl-2H [1]-benzopyran-2-yl)carboxamide
25) N-(2,4,5-trimethylphenyl)-(6-acetoxy-7-tert-butyl-3,4-dihydro-2-methyl-2H [1]-benzopyran-2-yl) carboxamide
26) N-(2,4,5-trimethylphenyl)-(6-hydroxy-7-tert-butyl-3,4-dihydro-2-methyl-2H [1]-benzopyran-2-yl) carboxamide
27) N-(2,4,5-trimethylphenyl)-(6-acetoxy-7-tert-butyl-3,4-dihydro-2-methyl-2H [1]-benzopyran-2-yl) acetamide and 28) N-(2,4,5-trimethylphenyl)-(6-hydroxy-7-tert-butyl-3,4-dihydro-2-methyl-2H [1]-benzopyran-2-yl) acetamide;

the enantiomers or diastereoisomers thereof, and the addition salts thereof with a pharmaceutically acceptable base.

Among the pharmaceutically acceptable bases which may be used to form an addition salt with the compounds of the invention, mention may be made, by way of non-limiting examples, of sodium, potassium, calcium or aluminium hydroxide, alkali metal or alkaline-earth metal carbonates, and organic bases such as triethylamine, benzylamine, diethanolamine, tert-butylamine, dicyclohexylamine and arginine.

The compounds of formula (I) are known as antioxidants and their preparation is described in EP 512,899.

The compounds of formula (I) possess very advantageous pharmacological properties. They have in particular shown a very powerful inhibitory capacity on the $Na^+$-independent $Cl^-/HCO_3^-$ exchanger (referred to hereinbelow as AE (for "Anion Exchanger"). It is also possible to use, where appropriate, a selectivity of the compounds of formula (I) for one or other of the 3 isoforms of the AE doubled or not from a tissue selectivity for a given isoform. This selectivity makes it possible to guarantee a specificity in the therapeutic action with a better efficacy/safety ratio.

The pharmacological evaluation of the compounds of formula (I) made it possible in particular to establish that the compounds of formula (I) are in particular useful for producing pharmaceutical compositions intended for the prevention and treatment of:

1—pathologies of the gastrointestinal tract, for example gastroduodenal ulcers, states of gastric acid hypersecretion (reflux oesophagitis, Zollinger-Ellison syndrome) and travel sickness.

Indeed, gastric parietal cells possess a basolateral AE (type AE2) whose activity is essential for maintaining the gastric acid secretion by apical $H^+/K^+$ ATPase (Muallem S. et al. J. Biol. Chem. 1988, 263: 14703–14711) and the epithelial cells of the colon possess an apical AE which is involved in the secretion of water and bicarbonate, this AE being the target of the cholera toxin.

2—Bone pathologies, for example bone modification disorders, in particular osteoporosis and Paget's disease, and inflammatory diseases with destruction of the bones, in particular arthritis.

Indeed, osteoclasts, the fundamental cells involved in bone resorption, possess a basolateral AE whose activity is essential for maintaining osteoclastic acid secretion by the "vacuolar-type" apicat $H^+$-ATPase located at the brush border, this acid secretion being essential for the destruction of the bone matrix by osteoclasts (Teti A. et al. J. Clin. Invest. 1989, 83: 227–233 and Hall T. J. et al. Calcif. Tissue Int. 1989, 45: 378–380).

3—Central pathologies and in particular cerebral oedemas of ischaemic or traumatic origin.

Indeed, astrocytes possess a $Cl^-$ influx AE facilitator in the cell, which is involved in the constitution of astrocytic oedema (Mellegard P. et al. Acta Neurochir., 1994, 60: 34–37). An AE (type AE2) is also present in the choroid plexus and allows the secretion of cerebrospinal fluid (Lindsey A. E et al P.N.A.S. USA 1990, 87: 5278–5282). The existence of a neuronal AE (AE3) allows action on neuronal development and maturation (Raley-Susman K. M. et al Brain Res. 1993, 614: 308–314).

4—Renal pathologies and in particular disorders of the acid-base equilibrium (conditions of acidosis and alkalosis) and of the hydroelectrolytic equilibrium as well as of nephropathies, in particular diabetic nephropathy.

Indeed, AE plays an important role in collecting tubes, a fundamental segment for the regulation of the acid-base equilibrium (Schuster V.L. Annu. Rev. Physiol. 1993, 55: 267–288). There is, in particular, a basolateral AE (AE1) in the α intercalary cells ("acid secreting" cells) involved in the acidification of the urine and an apical AE in the β intercalary cells ("base secreting" cells) involved in the basification of urine (Weiner I. D. et al. Am. J. Physiol 1994, 267: F952–F964). There is also an AE in mesangial cells, whose activity is regulated by growth factors (Ganz M. B. et al. Nature 1989, 337: 648–651).

5—Cardiovascular pathologies: ischaemia, angina, arrhythmias, cardiac insufficiency, hypertension, cardiovascular hypertrophy/hyperproliferation states (atherosclerosis, restenosis).

Indeed, the beneficial action of the compounds of formula (I) and in particular their importance in cardiovascular protection and restoration involves the cardiomyocytic AE (AE3) which is activated under conditions of myocardial ischaemia and contributes to the intracellular acidification as an addition to the metabolic acidification already present during ischaemia (Yannoukakos D. et al. Circ Res. 1994, 75: 603–614) various mediators, increased under ischaemic conditions (for example ATP and catecholamines) also possibly activating the AE (Pucéat M. et al. J. Physiol. 1991, 444: 241–256 and Désilets H. et al. Circ. Res. 1994, 75: 862–869). It is also known that AE is regulated by growth factors (Ganz M. B. et al. Nature, 1989,337: 648–651) and exhibits hyperactivity in the erythrocytes of a person suffering from hypertension (Alonso A. et al. Hypertension 1993, 22: 348–356).

6—Mucoviscidosis.

7—Pulmonary pathologies, on account of the presence of an AE (AE2) which regulates the intracellular pH on the basolateral surface of alveolar epithelial cells (Lubman R. L. et al. Am. J. Respir. Cell. Mol. Biol. 1995, 12: 211–219).

8—Diabetes (insulin secretion) (Sheperd R. M. et al. J. Biol. Chem 1995, 270: 7915–7921 and Sheperd R. M. et al. Diabetologia 1995, 38: A119, abstract 461) and diabetic complications, in particular ocular pathologies of diabetes such as retinopathy and sensitive and motor neuropathies such as diabetic gastroparesis.

9—Cytotoxicity induced by anti-cancer drugs, such as adriamycin (Asaumi J-I et al. Anticancer Research, 1995, 15: 71–76).

10—And Alzeimer's disease (Renkawek K et al. Neuroreport, 1995, 6: 929–932).

The invention also relates to the use of the compounds of formula (I) for the production of pharmaceutical compositions intended for the prevention and treatment of pathologies of the gastrointestinal tract, bone pathologies, central pathologies and in particular cerebral oedemas of ischaemic or traumatic origin, renal pathologies and in particular disorders of the acid-base equilibrium (acidosis and alkalosis conditions) and of the hydroelectrolytic equilibrium, as well as nephropathies, cardiovascular pathologies, mucoviscidosis, pulmonary pathologies, diabetes and diabetic complications, cytotoxicity induced by anti-cancer drugs and Alzheimer's disease.

The compounds of formula (I) have also shown themselves to be useful for the production of pharmaceutical compositions intended for hyperproliferation conditions, for example in the context of scars and repair tissue, AE being involved in the regulation of cell growth (Ganz et al. Nature 1989, 337: 648–651).

The invention also covers the use of the compounds of formula (I) as pharmacological tools in the pharmacological field of the $Na^+$-independent $Cl^-/HCO_3^-$ exchanger.

In particular, the invention covers the use of the compounds of formula (I) as pharmacological tools:

in order to detect the expression, for example tissue expression, of the AE, in order to perform AE binding studies, in order to identify and localize new isoforms of AE, in order to clone, sequence and express the AE.

The subject of the present invention is also the pharmaceutical compositions containing one of the derivatives of formula (I), or one of the addition salts thereof with a pharmaceutically acceptable base, in combination with one or more pharmacologically acceptable excipients or vectors.

Among the pharmaceutical compositions of the invention which may be mentioned by way of example, and in a limiting manner, are those which are suitable for oral, parenteral, nasal, rectal, perlingual, ocular or pulmonary administration and in particular injectable preparations, aerosols, eye drops or nasal drops, plain, film-coated or sugar-coated tablets, gelatin capsules, wafer capsules, suppositories, creams, ointments and dermal gels.

The ingredients present in the pharmaceutical composition are chosen, for example, from:

a) diluents, such as lactose, dextrose, sucrose, mannitol, sorbitol, cellulose and glycerol;

b) lubricants, such as silica, talc, stearic acid and the magnesium and calcium salts thereof, and polyethylene glycol;

c) binders, such as aluminium magnesium silicate, starch, gelatin, tragacanth, methylcellulose, sodium carboxymethylcellulose and polyvinylpyrrolidone;

d) disintegrating agents, such as agar, alginic acid and the sodium salt thereof, and effervescent mixtures; and e) absorbing agents, dyes, seasonings and sweeteners.

The injectable solutions are preferably aqueous isotonic solutions or suspensions and the suppositories are advantageously prepared from fatty emulsions or suspensions.

The compositions may be sterilized and/or contain adjuvants such as preserving agents, wetting agents, solubilizing agents or emulsifying agents, salts for adjusting the osmotic pressure or buffers.

The appropriate dosage varies according to the sex, age and weight of the patient, the route of administration, the nature of the complaint and treatments which may be associated therewith, and ranges between 0.1 mg and 1 g per 24 hours, for example between 1 and 100 mg per 24 hours, more particularly between 10 and 50 mg per 24 hours, for example 20 mg per 24 hours.

The examples which follow illustrate the invention without limiting it in any way.

Example A: MEASUREMENT OF THE ACTIVITY OF THE $Na^+$-INDEPENDENT $Cl^-/HCO_3^-$ EXCHANGER IN VENTRICULAR CARDIOMYOCYTES ISOLATED FROM RAT HEART The study is performed on ventricular cardiomyocytes isolated from rat heart by enzymatic dissociation. The intracellular pH of a single cell is measured by the fluorescent label carboxy-SNARF-1 whose fluorescence depends on its state of protonation (Buckler K. J. et al. Pflügers Archiv, 1990, 417: 234–239). The cells are "charged" beforehand with SNARF-1-AM (esterified and permeating form of the label) and the intracellular fluorescence of SNARF is monitored using an inverted microscope equipped with epifluorescence. The measurements are converted into pH using a calibration file.

The activity of the $Na^+$-independent $Cl^-/HCO_3^-$ exchanger is studied after activation by induction of an alkaline charge of the cells by the acetate method (Roos A et al. Physiol. Rev., 1981, 61: 296–434).

The activities of the $Na^+/H^+$ exchange and of the $Na^+/HCO_3^-$ cotransport are studied after activation by induction of an acid charge of the cells by the ammonium method (Boron W. F. et al. J. Gen. Physiol., 1976, 67: 91–112).

The compounds according to the invention are used at concentrations of $10^{-11}$ to $10^{-5}M$ and their $IC_{50}$ (50% inhibitory concentration) is calculated for each ion transporter. In parallel, the effects of the molecules on the intracellular intrinsic buffer power and the intracellular resting pH are determined.

The compounds of formula (I) proved to possess a powerful capacity to inhibit the Na+-independent $Cl^-/HCO_3^-$ exchanger. For example, the compound Example 14 is a selective inhibitor of the $Na^+$-independent $Cl^-/HCO_3^-$ exchanger with an $IC_{50}$ of about $10^{-10}M$.

Example B: GASTROINTESTINAL ULCER

On a culture of rabbit parietal cells: the activity of the AE and the acid secretion are measured under basal conditions or conditions of stimulation by secretagogues (Muallem S. et al., J. Biol. Chem., 1988, 263: 14703–14711).

Stress ulcer in rats: the model combines immobilization (containing box) and partial immersion of the rat in water at 22° C. for 6 hours. The severity of the gastric lesions is assessed in control rats or rats treated preventively with the compounds used according to the invention 30 minutes before exposure to the stress (Takagi K. et al., Japan J. Pharmacol. 1968, 18: 9–18).

Example C: DISORDERS OF BONE MODIFICATION

On a culture of hen osteoclasts: the activity of the AE and the acid secretion are measured (Teti A et al, J. Clin. Invest., 1989, 83: 227–233).

Test of in vitro bone resorption: osteoclasts from newborn rabbits are placed in contact with cow bone slices and incubated for 6 hours with the compounds used according to the invention. After incubation, each bone slice is examined in order to evaluate the intensity of the bone resorption (Chambers T. J. et al. Endocrinology, 1985, 116: 234–239).

Example D: CEREBRAL OEDEMA

On a culture of rat astrocytes: the activity of the AE is measured (Mellegard P. et al. Acta Neurochir., 1994, 60: 34–37).

On a culture of rat astrocytes: the astmcyte swelling induced by in vitro hypoxia is measured: the study is performed on astrocytes in primary culture obtained from the cerebral cortex of newborn Sprague Dawley rats subjected to hypoxia for 18 hours. The anti-oedematous effect is mainly studied by measuring the cell volume in the presence of radioactive 3-O-methyl-glucose and the extracellular activity of lactate dehydrogenase, a membrane damage marker (Kimelberg H. K. et al. Mol. Chem. Neuropath., 1989, 11: 1–31).

Example E: MYOCARDIAL ISCHAEMIA

Ischaemia-reinfusion model on isolated rat heart: the isolated rat heart is infused by the Langendorff method. A local ischaemia with a duration of 10 minutes is obtained by ligature of the left coronary artery, followed by a period of reinfusion by removal of the ligature. The functional parameters (coronary flow, left intraventricular pressure and heart rate) are measured every two minutes and the rhythm disorders are evaluated on reinfusion. The test compounds are infused throughout the ischaemia-reinfusion sequence. (Rochette L. et al, Clin. Exp. Theory. Practice, 1987, A9: 365–368).

Example F: CARDIOVASCULAR STUDY

The compounds are tested at a concentration of 0.1 μM in a solution of DMSO in Krebs buffer (0.01% v/v) on arrhythmias. 6 isolated rat hearts were used for the test compound and 6 for the control. An infusion by the Langendorff method is performed (Rees S. A. and Curtis M.J.J. Card. Pharmacol. 1995, 26: 280–288).

The preliminary results (n=6) show that the compound of Example 14 makes it possible to reduce the incidence of ventricular fibrillation observed during the ischaemia by 50%, in comparison with the control hearts. It thus possesses cardioprotective activity. Similarly, this compound reduces the incidence of ventricular fibrillation observed during reinfusion by 50%.

It thus turns out that the compound of the invention possesses good activity on the cardiovascular system. It especially possesses powerful antifibrilating activity.

Example G: PHARMACEUTICAL COMPOSITION: TABLETS

Tablets containing a 20 mg dose of N-(2,4,5-trimethylphenyl)-(6-hydroxy-3,4-dihydro-2,5,7,8-tetramethyl-2H[1]-benzopyran-2-yl)carboxamide.

Preparation formula for 1000 tablets

N-(2,4,5-Trimethylphenyl)-(6-hydroxy-3,4-dihydro-2,5,7, 8-tetramethyl-2H [1]-benzopyran-2-yl)carboxamide +tm 20 g
Wheat starch +tm 240 g
Lactose +tm 180 g
Magnesium stearate +tm 2,0 g
Silica +tm 0,8 g
Hydroxypropylcellulose +tm 2,0 g

We claim:

1. A method of treating a gastric ulcer or osteroporosis disorder associated with the $Na^+$-independent $Cl^-/HCO_3^-$ exchanger in a mammal comprising the step of administering to the said mammal an amount of a compound selected from the group consisting of those of formula (I):

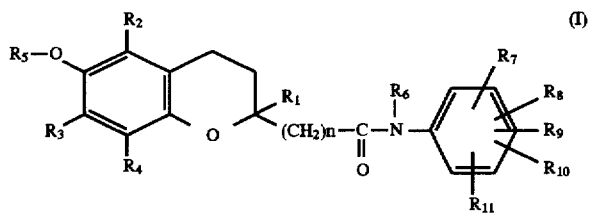

in which
n represents 0 or 1, $R_1$, $R_2$, $R_3$ and $R_4$, which are identical or different, represent, independently of each other, hydrogen or alkyl;

$R_5$ represents hydrogen or a radical selected from the group consisting of alkyl, alkylcarbonyl, alkoxyalkyl, alkoxycarbonyl, alkoxycarbonylalkyl, and carboxyalkyl;

$R_6$ represents hydrogen or a radical selected from the group consisting of alkyl, phenyl, and phenylalkyl;

$R_7$, $R_8$ and $R_9$ represent, independently of each other, a radical selected from the group consisting of halogen, alkyl, alkyl substituted with halogen, alkoxy, hydroxyl, alkoxycarbonyl, and carboxyl;

and $R_{10}$ and $R_{11}$ represent, independently of each other, hydrogen or a radical selected from the group consisting of halogen, alkyl, alkyl substituted with halogen, alkoxy, hydroxyl, alkoxycarbonyl, and carboxyl;

enantiomers and diastereoisomers thereof and an addition salt thereof with a pharmaceutically-acceptable base, it being understood that the terms "alkyl" and "alkoxy" denote linear or branched groups of 1 to 8 carbon atoms;

which is effective for alleviating the said disorder.

2. A method of claim 1, in which the compound is selected from the group consisting of those of the formulae (I/a) and (I/b):

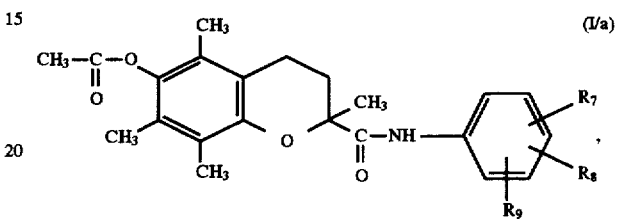

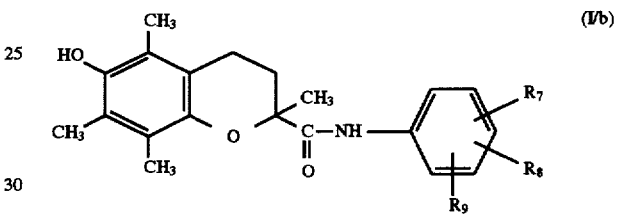

enantiomers and diastereoisomers thereof, and an addition salt thereof with a pharmaceutically-acceptable base.

3. A method of claim 1, wherein the compound is N-(2, 4,6-trimethylphenyl)-(6-acetoxy-3,4-dihydro-2,5,7,8-tetramethyl-2H [1]-benzopyran-2yl)carboxamide.

4. A method of claim 1, wherein the compound is N-(3, 5-dichloro-4-hydroxyphenyl)-(6-hydroxy-3,4-dihydro-2, 5,7, 8-tetramethyl-2H[1]-benzopyran -2-yl)carboxamide.

5. A method of claim 1, wherein the compound is N-(2, 4,5-trimethylphenyl)-(6-hydroxy-3,4-dihydro-2,5,7,8-tetramethyl-2H [1]-benzopyran-2-yl)carboxamide.

6. A method of claim 1, wherein the compound is present in a pharmaceutical composition together with one or more pharmacologically-acceptable excipients.

* * * * *

UNITED STATES PATENT AND TRADEMARK OFFICE
CERTIFICATE OF CORRECTION

PATENT NO. : 5,703,118
DATED : Dec. 30, 1997
INVENTOR(S) : L. Durand, J.P. Babingui, C. Moulin, S. Robert-Piessard, G. LaBaut, E. Scalbert, D.H. Caignard, P. Renard It is certified that error appears in the above-indentified patent and that said Letters Patent is hereby corrected as shown below:

Column 9, lines 9 through 16: Delete, in each line, "+tm".

Signed and Sealed this

Seventh Day of April, 1998

Attest:

BRUCE LEHMAN

Attesting Officer

Commissioner of Patents and Trademarks